(12) United States Patent
Kwon et al.

(10) Patent No.: US 6,808,724 B2
(45) Date of Patent: Oct. 26, 2004

(54) **ARTEMISOLIDE COMPOUND ISOLATED FROM THE AERIAL PARTS OF *ARTEMISIA SYLVATICA*, ISOLATION METHOD, AND USE THEREOF**

(75) Inventors: Byoung-Mog Kwon, Daejeon (KR); Kwang-Hee Son, Daejeon (KR); Dong-Choi Han, Daejeon (KR); Jong-Han Kim, Kyoungnam (KR); Hyun-Mi Kang, Choongbuk (KR); Sun Bok Jeon, Choongbuk (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 10/352,836

(22) Filed: Jan. 28, 2003

(65) Prior Publication Data

US 2004/0044068 A1 Mar. 4, 2004

(30) Foreign Application Priority Data

Aug. 30, 2002 (KR) .................................. 10-2002-52017

(51) Int. Cl.[7] ....................... A61K 35/78; A61K 31/34; A61K 31/335; C07D 493/00; C07D 313/06
(52) U.S. Cl. ..................... 424/740; 514/462; 514/468; 549/264; 549/268; 549/297; 549/263
(58) Field of Search .................. 424/740; 514/462, 514/468; 549/263, 268, 297, 264

(56) References Cited

U.S. PATENT DOCUMENTS 6,020,365 A * 2/2000 Adekenov ................... 514/468

OTHER PUBLICATIONS

Cox, Adrienne D. et al., The CAAX Pepidomimetic Compound B581 Specifically Blocks Farnesylated, but Not Geranylgeranylated or Myristylated, Oncogenic Ras Signaling and Transformation, *The Journal of Biological Chemistry*, Jul. 29, 1994, vol. 269, No. 30, pp. 19203–19206.

(List continued on next page.)

*Primary Examiner*—Ba K. Trinh
*Assistant Examiner*—Taylor V. Oh
(74) *Attorney, Agent, or Firm*—Jones Day

(57) ABSTRACT

The present invention relates to a novel compound isolated from *Artemisia Sylvatica*, expressed by the formula 1, a method of isolation, and its use thereof, and more particularly to a novel compound isolated from *Artemisia Sylvatica*, a method of isolation, and its use in inhibiting farnesyl transferase activity, which is essential for activating Ras oncogene, and repressing cancer cell growth.

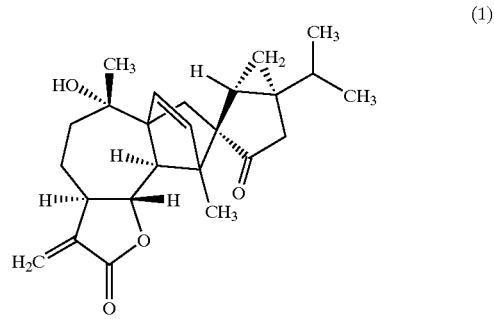

(1)

3 Claims, 3 Drawing Sheets

UV spectrum of Artemisolide

OTHER PUBLICATIONS

Goldstein, Jospeh L. et al., Nonfarnesylated Tetrapeptide Inhibitors of Protein Farnesyltransferase, *The Journal of Biological Chemistry*, Aug. 25, 1991, vol. 266, No. 24, pp. 11575–15578.

Qian, Yimin et al., Farnesyltransferase as a Target for Anticancer Drug Design, *Biopoly* 43:1997, pp. 25–41.

Reuter, Christoph W. et al., Targeting the Ras signaling pathway: a rational, mechanism–based treatment for hematologic malignancies? *Blood*, Sep. 1, 2000, vol. 96, No. 5, pp. 1655–1669.

Glomset, John A. et al., Role or Protein Modification Reactions in Programming Interactions Between Ras–Related Gtpases and Cell Membranes, *Annu. Rev. Cell. Biol.*, 1994, pp. 181–205.

Lebowitz, Peter F. et al., Farnesyl Transferase Inhibitors Induce Apoptosis of Ras–transformed Cells Denied Substratum Attachment, *Cancer Research*, Feb. 15, 1997, pp. 708–713.

Moasser, Mark M. et al., Farnesyl tansferase inhibitors cause enhanced mitotic sensitivity to taxol and epothilones, *Proc. Natl. Acad. Sci. USA*, Feb. 1998, Fol. 95, pp. 1369–1374.

Newman, David J. et al., The influence of natural products upon drug discovery, *Nat. Prod. Rep.*, Dec. 20, 1999, pp. 215–234.

Kim, Jong Han et al., New sesquiterpene–monoterpene lactone, artesmisolide, isolated from *Artemisia argyi, Tetrahedron Letters*, Aug. 26, 2002, vol. 43, Issue 35, pp. 6205–6208.

* cited by examiner

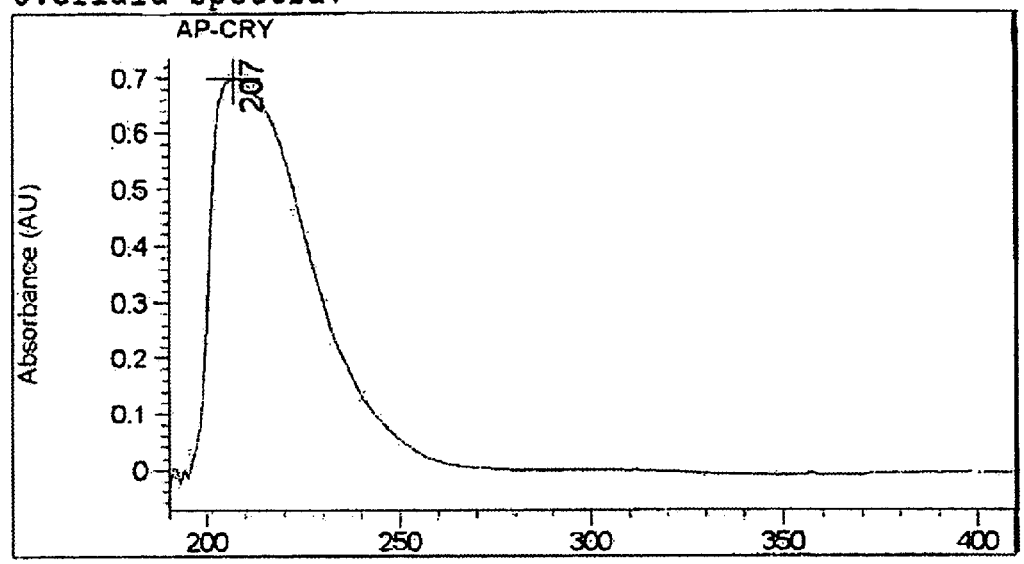
Fig. 1. UV spectrum of Artemisolide
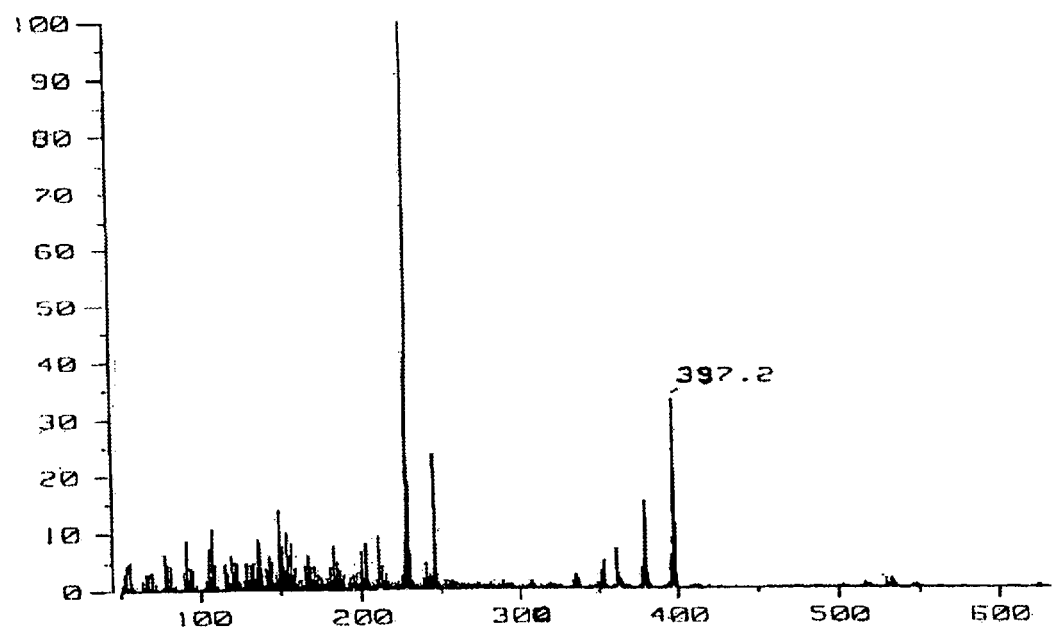
Fig. 2. Mass spectrum of Artemisolide

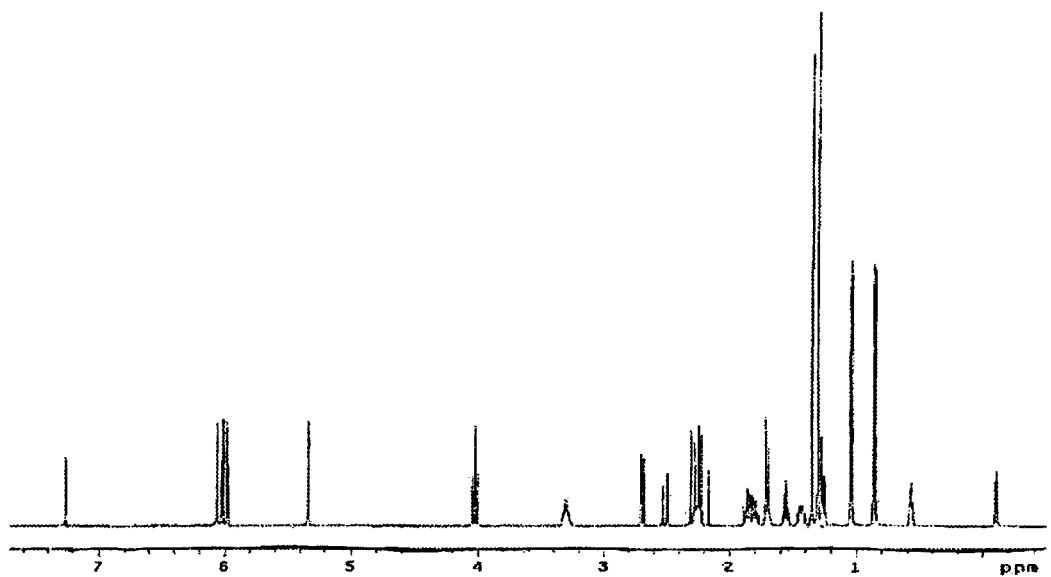
Fig. 3. 1H-NMR spectrum of Artemisolide
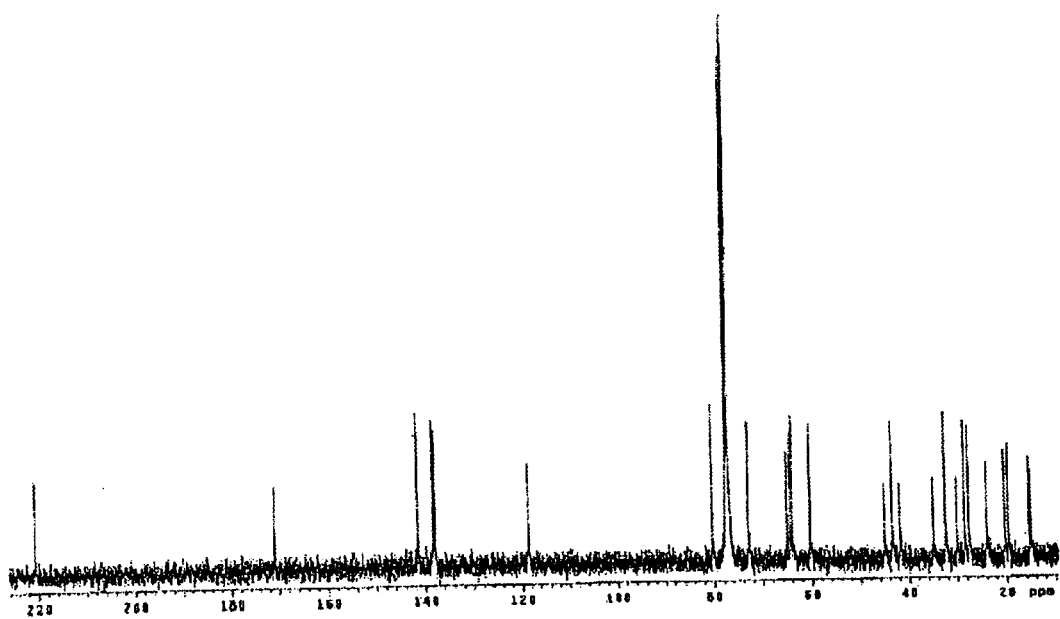
Fig. 4. 13C-NMR spectrum of Artemisolide

ARTEMISOLIDE COMPOUND ISOLATED FROM THE AERIAL PARTS OF ARTEMISIA SYLVATICA, ISOLATION METHOD, AND USE THEREOF

BACKGROUND OF THE INVENTION

1. Field of the Invention

The present invention relates to a novel compound isolated from *Artemisia Sylvatica*, isolation method, and use thereof, and more particularly, to a novel compound isolated from *Artemisia Sylvatica*, which is expressed by the formula 1, a method of isolation thereof, and its use of inhibiting farnesyl transferase activity, which is essential for activating Ras oncogene and repressing cancer cell growth.

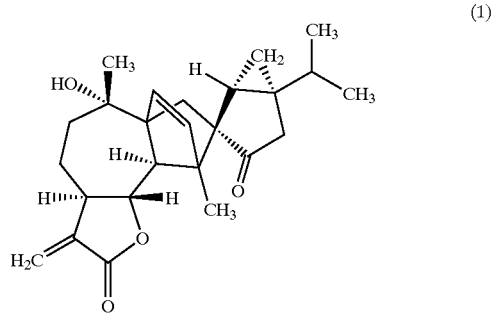

(1)

2. Description of the Related Art

The exact causes of most cancers have not been identified yet, but researches have been only able to reveal a few carcinogens or carcinogenic factors so far. Innate carcinogenic factors residing in an individual can be turned on during his growth and cause a mutation when subjected to various carcinogenic environments, and may ultimately develop into a cancer. Therefore, it is very important to know the cause of a cancer in order to prevent and detect onset of an oncocogenesis from cancer-vulnerable groups via early diagnosis.

Three major treatments for cancers are surgery, radiotherapy, and chemotherapy. Besides, there are immunotherapy, hormonotherapy, or biological therapies (the biological therapies include transition inhibition, CDK inhibition, blood-vessel formation inhibition, and signal-transfer inhibition, etc.). One or more therapies may be used depending on the type of cancers. The kind of cancer, its location, transition, age and physical condition of a patient, and other factors are considered in selecting the most appropriate treatment.

Over the last decade, there have been outstanding research results on normal cells and mutated cells. In particular, regarding the oncogenic functions, how the normal proto-oncogene function, how they are changed into oncogenes, how the signal transfer regulates division, and differentiation and death of cells are now well elucidated. In short, cancers can be described as cells that are divided abnormally, whose growth and differentiation are not under control. In normal cells, cell division is orchestrated by an elaborate signal regulation of the cell's inner and external growth factors. However, in cancer cells, at least one of the growth regulation factors remains activated (switched on) or deactivated (switched off). These cell division-related signals are transferred via the protein-protein interaction.

Cancers are known to develop by mutation of these cell division-related proteins. Among the cancer-related proteins, the Ras protein accounts for about 30% of all human cancers.

The Ras protein, which plays the most important role in signal transfer of cell growth regulation factors, is composed of 188–189 amino acids. Its molecular weight is 21 kDa and it can be bound to guanine nucleotides (GDP or GTP). The Ras protein transfers a cell signal to regulate proliferation and differentiation of cells. Like many other G-proteins, the Ras protein acts as the signal transferer when bound to GTP (switched "on"), and it is deactivated (switched "off") when GTP is hydrolyzed to GDP by GAP (GTPase activating protein).

The Ras protein is located in the plasma membrane, bound to lipids, and transfers signal to the next stage. Cysteine (Cys-186), the 186th amino acid of the Ras protein is covalently bonded to the lipid (carbon number=15 or 20) by thioester linkage. The lipid has its own GTPase activity and is triggered by GAP and GTPase activation proteins. As such, the Ras protein is bound to the inner surface of the plasma membrane. In this process, binding with GTP and hydrolysis mediates regulation of cell growth. The cysteine, where this lipidation takes place, is the 4th residue of the Ras protein from the carboxyl or C-terminal. After two aliphatic amino acids comes methionine or serine. The lipid transferase transfers $C_{15}$ or $C_{20}$ lipids to the "Cys-AAX motif". The $C_{15}$-carbon isoprenoid group (farnesyl group) is transferred by farnesyltransferase; and if the X, the last residue of the Ras protein, is leucine, a special soluble enzyme transfers the $C_{20}$-carbon isoprenoid group (geranylgeranyl group) [Joseph L. Goldstein, et al., "Nonfarnesylated Tetrapeptide Inhibitors of Protein Farnesyltransferase" *The Journal of Biological Chemistry*, 266, 15575–15578, (1991); John A. Glomset and Christopher C. Farnsworth, "Role of Protein Modification Reactions in Programming Interactions between RAS-related GTPases and Cell Membranes", *Annu. Rev. Cell Biol.*, 10, 181–205, (1994)].

The endoprotease, which has affinity to lipid-bound substrate, catalyzes proteolytic cleavage of -AAX peptide from the lapidated -CysAAX sequence, while the methyl transferase catalyzes methylesterification of the cleaved cysteine residue to the carboxyl group. In doing so, the —COOH terminal of the Ras protein becomes lipophilic and is bound to the membrane. Thus, it can be readily accessed to the Ras protein. All the lipids bound to the Ras protein are trans FPPs (farnesyl pyrophosphates) formed from mevalonate intermediate during cholesterol biosynthesis.

This consecutive lipidation of -AAX peptide hydorolysis and methylation is called the post-translation process. The development of a drug that can effectively regulate these reactions, i.e. the signal transfer process, will lead to development of new anticancer drug. Even if the Ras protein has been mutated for a long time in the activated form, it should be fixed to the membrane by prenylation (farnesyl or geranylgeranyl lipid) to be able to transfer signals required for cell growth or differentiation. And, the regulation of the three enzymes can be the target site of inhibiting signal transfer of the Raf protein [Yimin, Q.; Sebti, S. M; Andrew, D. H. *Biopoly.* 1997, 43, 25–41, Christoph, W. M.; Morgan, M. A.; Lothar, B. *Blood.* 2000, 96, 1655–1669., Cox A. D.; Garcia, A. M.; Westwick, J. K.; Kowalczyk, J. J.; Lewis, M. A.; Brenner, D. A.; Der, C. J. *J. Biol. Chem.* 1994, 269, 19203–19206., Lebowitz P. F.; Sakamuro, D.; Prendergast, G. C. *Cancer Res.* 1997, 57, 708–713., Mark, M.; Moasser M. M.; Sepp-Lorenzio, L.; Kohl, N. C.; Oliff, A.; Balog, A.; Su, D. S.; Danishefsky, S. J.; Rosen, N. *Proc. Natl. Acad. Sci. USA.* 1998, 95, 1369–1374.]

For the raw material of this anticancer drug, medicinal plants like yaw tree or periwinkle are used. The active ingredients of these plants were identified as paclitaxel (product name=Taxol) and vinblastine [*Natural Product Report* 2000, 17, 215–234].

SUMMARY OF THE INVENTION

The inventors discovered a compound with anticancer activity from *Artemisia Sylvatica* in the process of searching for anticancer substances from medicinal plants. We isolated the compound and analyzed its structure to realize that it is a new compound expressed by the formula 1.

An object of this invention is to provide a new compound isolated from *Artemisia Sylvatica*, isolation method, and use thereof.

Another object of this invention is to provide a drug composition for prevention and treatment of cancers, containing the new compound as an active ingredient.

BRIEF DESCRIPTION OF THE DRAWINGS

FIG. 1 is a UV-visible absorption spectrum for the chemical compound expressed by Formula 1.

FIG. 2 is a mass spectrum for the chemical compound expressed by Formula 1.

FIG. 3 is a $^1$H-NMR spectrum for the chemical compound expressed by Formula 1.

FIG. 4 is a $^{13}$C-NMR spectrum for the chemical compound expressed by Formula 1.

DETAILED DESCRIPTION OF THE INVENTION

Figure 5:
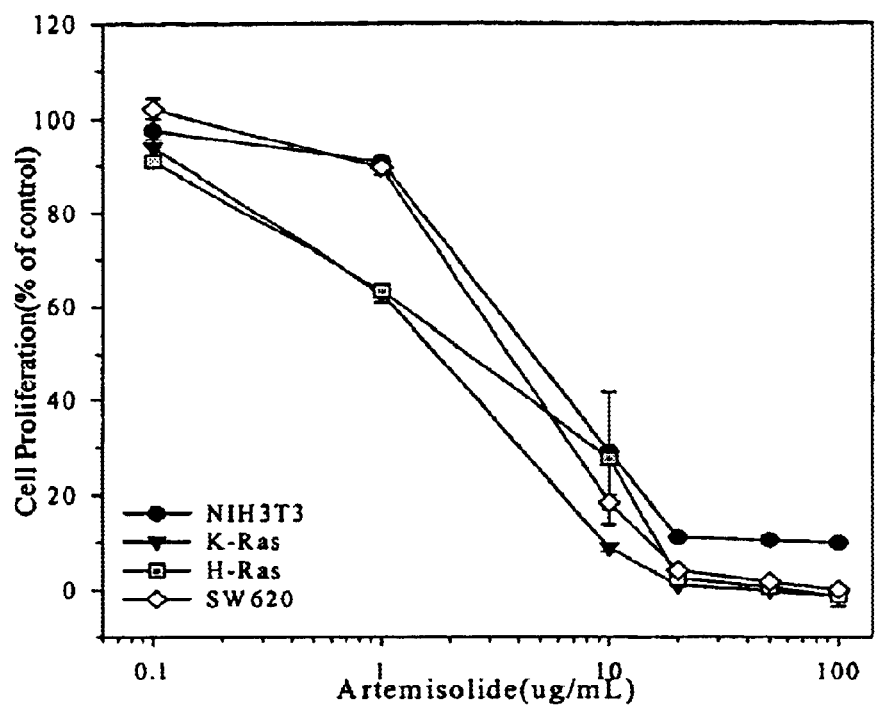
FIG. 5 is a graph that shows the inhibition effect on solid tumor cell growth of the chemical compound expressed by Formula 1.

The present invention relates to a new compound isolated from *Artemisia Sylvatica*, which is expressed by the formula 1, a method of isolation, and its use thereof.

(1)

[Chemical structure of Formula 1]

The present invention also includes a drug composition for prevention and treatment of cancers, containing the compound as active ingredient.

Hereunder is given a more detailed description of this invention.

This invention relates to a new compound isolated from *Artemisia Sylvatica*, which is expressed by Formula 1, isolation method thereof, and its use of inhibiting farnesyl transferase activity, which is essential for activating Ras oncogene, and repressing cancer cell growth.

Dry leaves and stems of *Artemisia Sylvatica* are extracted in an organic solvent and filtrated to obtain liquid extract. For the organic solvent, 10–100% of methanol, ethanol, propanol and butanol can be used. However, 100% of methanol is preferred. This extract is condensed under reduced pressure and dissolved in ethyl acetate. Then, water is added to separate the extract. The inhibiting activity on farnesyl transferase is identified in the organic solvent layer. The organic solvent layer is condensed under reduced pressure. A column chromatography is carried out for this condensate to separate the active layer. For example, the condensate is put in a column, and mixture of hexane and ethyl acetate (composition varying in the range of 100:0–0:100) is added to remove the polar and non-polar substances. Then, active substance separated by 50:50 of hexane and ethyl acetate is partially purified. Another column chromatography (C18, silica gel, LH-20) is carried out to purify the obtained fraction. A thin-layer chromatography is carried out for the purified active fraction to separate the fraction with the most superior farnesyl transferase inhibition activity. This fraction is purified by high-pressure column chromatography (HPLC).

The structure of the obtained white powder compound was analyzed by NMR. The compound is expressed by Formula 1 (molecular formula=$C_{25}H_{32}O_4$; molecular weight=396.52). Physical and chemical properties of the compound is shown in Table 1.

TABLE 1

| Appearances | White crystal |
|---|---|
| Molecular Formula | $C_{25}H_{32}O_4$ |
| UV Absorption | 207 |
| Molecular Weight | 396.52 |
| Melting Point (° C.) | 200 |
| Soluble in | MeOH; acetone; EtOAc |
| Insoluble in | Hexane |

The anticancer activity of this compound was tested by growth inhibition on tumor cell lines and inhibition activity on farnesyl transferase. The compound was identified to be useful for anticancer drugs, and oncogene expression inhibitors.

Because this compound has anticancer activity and farnesyl transferase inhibition activity, it can be prepared into a pharmaceutical composition for prevention and treatment of cancers, using pharmaceutically available carriers. The $IC_{50}$ (concentration for inhibiting activity by 50%) value of this compound on farnesyl transferase is about 100 μg/ml. Because this compound represses expression of cancerous proteins like Ras protein by inhibiting their farnesylation, the pharmaceutical composition containing this compound can be useful for prevention and treatment of cancers related with cancerous proteins.

Said pharmaceutical composition can be prepared into single or multi administration drugs, including capsules, powders, granules, emulsions or non-oral administration drugs.

The pharmaceutical composition can be administered orally or non-orally. The administration dose is 2 mg to 15 mg, preferably 5 mg to 10 mg, per 1 kg of body weight a day. It can be administered once or several times. However, the administration dose may be different depending on the body weight, age, sex, physical condition, diet, administration time, administration method, excretion rate, and severity of disease of a patient. Since the compound of this invention is isolated and purified from *Artemisia Sylvatica*, which has long been used as herbal medicines, it is safe. It showed no acute toxicity in the animal test. The pharmaceutical composition containing the compound expressed by Formula 1 is very useful for anticancer drugs or oncogene expression inhibitors.

Hereunder is given a more detailed description of this invention, using examples. The following examples are to be illustrative of this invention and should not be construed as limiting the scope of this invention.

EXAMPLE 1

Isolation of New Compound from *Artemisia Sylvatica*

1 kg of leaves of *Artemisia Sylvatica* that grows wild in central Korea were crushed. After adding 2 l of 100% methanol, it was let alone for 48 hr at room temperature. Then, it was filtered to separate the liquid and the solid. The liquid was condensed under reduced pressure and 1 l of ethyl acetate was added to dissolve the condensate. Then, 1 l of water was added to separate the organic solvent layer from the water layer. For the dissolved fraction (organic solvent layer), farnesyl transferase inhibition activity was determined to identify that active substance(s) is(are) contained in the organic solvent layer.

The organic solvent layer was condensed under reduced pressure and dissolved in methylene chloride. The solution was added to silica gel (Merck, Art No. 9385) to adsorb the active substance. Nonpolar substances were removed by the first silica gel column chromatography, varying the hexane to ethyl acetate from 9:1 to 3:7. Then, the active fraction, eluted when the hexane to ethyl acetate ratio was 5:5, was separated. The obtained active fraction mixture was adsorbed in a C18 column and was eluted with methanol and water to obtain partially purified active substance. The substance was divided into several fractions by thin-layer chromatography. Among the fractions, the one that shows the highest activity was obtained by high-pressure liquid chromatography (HPLC), which is the compound of this invention. For the HPLC column, J'sphere ODS-H80 (250× 20 mm I.D.) of YMC was used. The active substance was eluted with a mixture containing 50–70% methanol and 50–30% water. The yield was about 20 mg per 1 kg of *Artemisia Sylvatica*.

EXAMPLE 2

Structure Analysis of the New Compound $^1$H, $^{13}$C, COSY, HMQC, HMBC and NOESY spectra were obtained by NMR (Varian UNITY 300 MHz, 500 MHz NMR) to determine the molecular weight and the molecular formula of the obtained compound. Also, UV absorption, IR(infrared) absorption and high-resolution MS analyses were carried out. To be specific, the UV absorption was measured by a UV-visible spectroscopy system (Agilent 8453, HEWLETT PACKARD); the IR absorption was measured by using a Digilab Division FTS-80 Spectrometer (Bio-Rad); and the high-resolution MS was carried out by using a mass spectrometer (JMS-HX 110A/X 100A). The X-ray analysis result after recrystallization was coincident with the spectra. The result is shown in FIGS. 1–4 and Table 2.

TABLE 2

| Atom No. | $^{13}$C-NMR, δ | $^1$H-NMR, δ |
|---|---|---|
| 1 | 80.27 | 4.0t(J=10.0Hz) |
| 2 | 65.07 | 2.67d(J=10.0Hz) |
| 3 | 63.96 | |
| 4 | 72.99 | |
| 5 | 34.98 | 1.83m |
| 6 | 24.01 | 2.24m |
|   |       | 1.41m |
| 7 | 43.40 | 3.29m |
| 8 | 141.50 | |
| 9 | 170.96 | |
| 10 | 60.27 | |
| 11 | 64.44 | |

TABLE 2-continued

| Atom No. | $^{13}$C-NMR, δ | $^1$H-NMR, δ |
|---|---|---|
| 12 | 41.78 | 2.23d(J=8.0Hz); 1.27d(J=8.0Hz) |
| 13 | 220.69 | |
| 14 | 45.02 | 2.49dd(J=2.4, 18.4Hz); 2.26dd(J=2.4, 18.4Hz) |
| 15 | 28.46 | |
| 16 | 27.59 | 1.23dd(J=3.6, 8.0Hz) |
| 17 | 138.35 | 6.0d(J=5.6Hz) |
| 18 | 137.99 | 5.97d(J=5.6Hz) |
| 19 | 15.45 | 0.55m; −0.12dd(J=3.6, 5.6Hz) |
| 20 | 118.64 | 6.04d(J=3.4 Hz); 5.31d(J=3.4Hz) |
| 21 | 30.07 | 1.29s |
| 22 | 15.04 | 1.35s |
| 23 | 32.44 | 1.54m |
| 24 | 19.64 | 0.84d(J=7.2Hz) |
| 25 | 20.35 | 1.02d(J=6.4Hz) |

Thus obtained substance is a white powder compound whose molecular formula is $C_{25}H_{32}O_4$ with the molecular weight of 396.52 and was named Artemisolide accordingly. Its structure is shown in the formula 1.

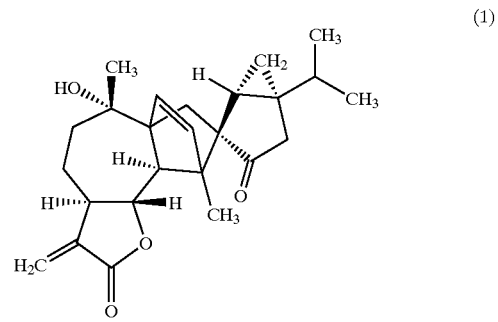

(1)

EXAMPLE 3

Anticancer Activity Test for the New Compound

NIH3T3 (mouse fibroblast), K-ras (K-ras gene transformed NIH3T3 cell), H-ras (H-ras gene transformed NIH3T3 cell) and SW620 (human colon cancer cell) solid tumor cell lines were cultured in 10% of bovine serum albumin or RPMI 1640 medium (containing L-glutamine and not containing sodium bicarbonate; Gibco Cat. No 31800-022) under 37° C. and 5% $CO_2$ condition. The subculture was carried out 2 times a week. The cells were separated from the wall using 0.5% of trypsin and 5.3 mM EDTA (ethylenediamine tetra acetic acid) dissolved in phosphate buffer solution (PBS). In each well of 96-well plate (Falcon), $3\times10^3$–$6\times10^3$ cells were added and cultured at 37° C. in the presence of 5% $CO_2$ of medium for 24 hr. The new compound was dissolved in dimethyl sulfoxide (DMSO) and diluted to the concentration required for the test. The final concentration of DMSO was set to be lower than 0.5%.

Figure 6:
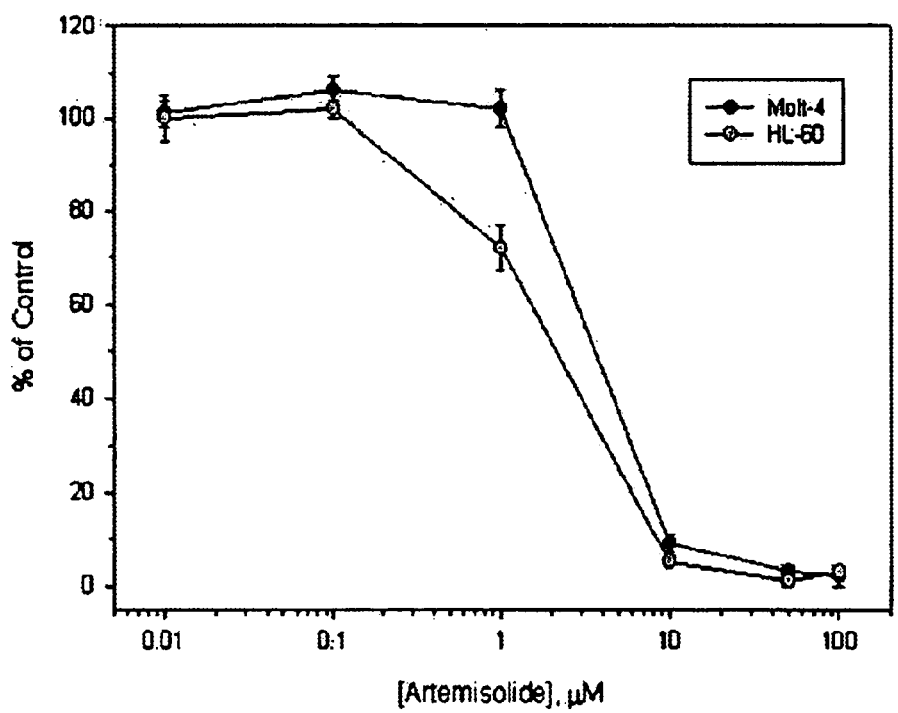
FIG. 6 is a graph that shows the inhibition effect on leukemia cell growth of the chemical compound expressed by Formula 1.

After removing all medium from the 96-well plate, 1 l of the new compound was added to each well. After 48 hr of culture, WST-1 was added to each well. Then the culture plate was placed for 3 hr at 37° C. in the presence of 5% $CO_2$. When the reaction was completed, light absorption at 450–690 nm was measured by using an ELISA reader to identify the cancer cell growth inhibition effect. The $GI_{50}$, the concentration when the cancer cell growth is inhibited by 50%, was about 5.5 μ/ml for the NIH3T3 cell, about 0.8 μg/ml for the K-Ras cell, 1.2 μg/ml for the H-Ras cell, 2.5 μg/ml for the SW620 cell, 3.2 μM for the Molt-4 cell, and about 1.5 μM for the HL-60 cell [FIGS. 5 & 6].

EXAMPLE 4

Determination of Farnesyl Transferase Inhibition Activity

100–150 g of brain was separated from a male rat (Sprague Dowley). It was washed with a physiological salt solution and homogenized. Then, farnesyl transferase enzymogen was separated by centrifuging and partially purifying the homogenate with a Q Sepharose Fast Flow Column. The enzyme activity was determined by scintillation proximity assay (SPA), using the $^3$H-farnesyl pyrophosphate (FPP) substrate.

To be specific, the method of Michael S. Brown, etc. (Yuval Reiss, Joseph L. Goldstein, Miguel C. Seabra, Patrick J. Casey and Michael S. Brown, 1990, Inhibition of Purified p21ras Farnesyl Protein Transferase by Cys-AAX Tetrapeptides, 62, 81–88) was modified a little. 10 µl of the sample liquid, 10 µl of analysis buffer solution (50 mM Tris-HCL pH7.5, 25 mM $MgCl_2$, 2 mM KCl, 5 mM DTT, 5 mM $Na_2HPO_4$, 0.01% Triton X-100), 20 µl of diluted $^3$H-FPP, 20 µl biotin-lamin B peptide and 40 µl of farnesyl transferase were mixed well and rendered to react for 30 min at room temperature. Then, 150 µl of SPA bead/stop reagent solution was added. The farnesylation level of biotin-lamin B peptide was measured by using a scintillation counter in CPM (counts per minute) unit. The farnesyl transferase activity inhibition was calculated via Equation 1.

$$\text{Inhibition Activity}(\%) = \frac{\text{CPM (sample)} - \text{CPM (blank sample)}}{\text{CPM (control sample)} - \text{CPM (blank sample)}} \quad \text{(Equation 1)}$$

In the above Equation 1, the blank sample is the one without an enzyme and an inhibitor sample; and the control sample is the one without an inhibitor sample. The farnesyl transferase inhibition activity was identified to be about 50% at 100 µg/ml.

EXAMPLE 5

Toxicity Test

The compound expressed by the formula 1 was dissolved in dimethyl sulfoxide (DMSO). The solution was diluted with water and administered to mice (10 heads per group) by 100 µg/kg. After 7 days, all mice were alive.

PREPARATION EXAMPLE 1

Preparation of Tablets

| Active ingredient | 10 g |
| Lactose | 70 g |
| Crystalline cellulose | 15 g |
| Magnesium stearate | 5 g |
| Total | 100 g |

The above ingredients were crushed, mixed and prepared into tablets by the direct tableting method. The weight of each tablet is 100 mg, and its active ingredient content is 10 mg.

PREPARATION EXAMPLE 2

Preparation of Powder

| Active ingredient | 10 g |
| Corn starch | 50 g |
| Carboxy cellulose | 40 g |
| Total | 100 g |

The above ingredients were crushed, mixed and prepared into powder. 100 mg of the powder was put into a hard capsule.

PREPARATION EXAMPLE 3

Preparation of Injection Drugs 200 mg of the new compound was dissolved in 200 mg of a hot physiological salt solution containing polyoxyethylene hydrogenated castro oil. The injection drug was prepared by diluting this solution 10 times.

As explained above, the pharmaceutical composition containing the new compound isolated from *Artemisia Sylvatica*, which is expressed by the formula 1, is very useful for anticancer drugs or oncogene expression inhibitors.

What is claimed is:
1. A purified compound of the formula 1

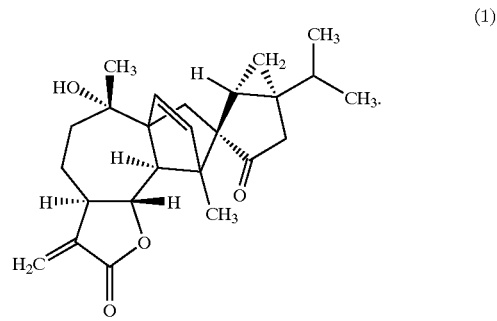

(1)

2. A method of isolating the compound of the formula 1 from *Artemisia Sylvatica* comprising the steps of:

1) extracting leaves and stems of *Artemisia Sylvatica* using an alcohol;

2) separating an active fraction from the alcohol extract by column chromatography;

3) eluting the active fraction to obtain a purified active substance; and 4) separating the most active fraction by thin-layer chromatography and purifying it by column chromatography (HPLC)
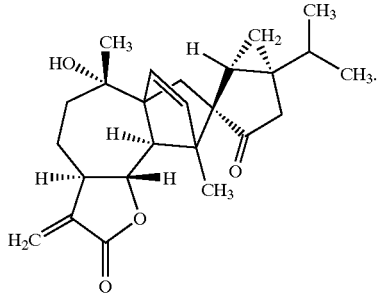
(1)
3. A pharmaceutical composition for treatment of leukemia and colon cancers comprising the purified compound of formula 1 and a pharmaceutically acceptable carrier
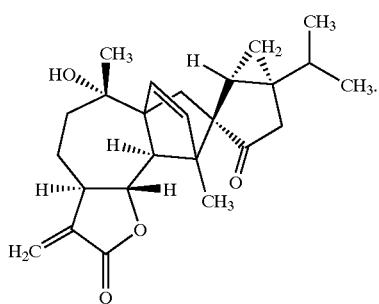
(1)
* * * * *